US012182998B2

(12) United States Patent
Arberet et al.

(10) Patent No.: US 12,182,998 B2
(45) Date of Patent: Dec. 31, 2024

(54) SELF-SUPERVISED MACHINE LEARNING FOR MEDICAL IMAGE RECONSTRUCTION

(71) Applicant: Siemens Healthineers AG, Erlangen (DE)

(72) Inventors: Simon Arberet, Princeton, NJ (US); Mariappan S. Nadar, Plainsboro, NJ (US); Mahmoud Mostapha, Princeton, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 373 days.

(21) Appl. No.: 17/652,528

(22) Filed: Feb. 25, 2022

(65) Prior Publication Data

US 2023/0274418 A1    Aug. 31, 2023

(51) Int. Cl.
*G06T 7/00* (2017.01)
*G01R 33/48* (2006.01)
*G16H 30/40* (2018.01)

(52) U.S. Cl.
CPC ........ *G06T 7/0012* (2013.01); *G01R 33/4818* (2013.01); *G16H 30/40* (2018.01); *G06T 2207/10088* (2013.01); *G06T 2207/20081* (2013.01); *G06T 2207/20084* (2013.01)

(58) Field of Classification Search
CPC ..................... G06T 7/00; G06T 7/0012; G06T 2207/10088; G06T 2207/20084; G06T 2207/20081; G06T 5/60; G01R 33/48; G01R 33/4818
See application file for complete search history.

(56) References Cited

U.S. PATENT DOCUMENTS

| 10,922,816 B2* | 2/2021 | Huang .................. G16H 30/40 |
| 2023/0245354 A1* | 8/2023 | Hamilton ............. G06V 10/776 |
| | | 382/131 |

OTHER PUBLICATIONS

Azizi, Shekoofeh, et al. "Big self-supervised models advance medical image classification." Proceedings of the IEEE/CVF International Conference on Computer Vision. Apr. 2021. pp. 1-19.
Defazio, Aaron, Tullie Murrell, and Michael Recht. "MRI banding removal via adversarial training." Advances in Neural Information Processing Systems 33 (2020): 1-11.
Desai, Arjun D., et al. "Noise2recon: A semi-supervised framework for joint MRI reconstruction and denoising." arXiv preprint arXiv:2110.00075 (2021).
Desai, Arjun D., et al. "Vortex: Physics-Driven Data Augmentations for Consistency Training for Robust Accelerated MRI Reconstruction." arXiv preprint arXiv:2111.02549 (2021). pp. 1-18.

* cited by examiner

*Primary Examiner* — Tuan H Nguyen

(57) ABSTRACT

For reconstruction in medical imaging, self-consistency using data augmentation is improved by including data consistency. Artificial intelligence is trained based on self-consistency and data consistency, allowing training without supervision. Fully sampled data and/or ground truth is not needed but may be used. The machine-trained model is less likely to reconstruct images with motion artifacts, and/or the training data may be more easily gathered by not requiring full sampling.

19 Claims, 2 Drawing Sheets

SELF-SUPERVISED MACHINE LEARNING FOR MEDICAL IMAGE RECONSTRUCTION

FIELD

This disclosure relates to medical image reconstruction, such as reconstruction in magnetic resonance (MR) imaging.

BACKGROUND

Magnetic resonance reconstruction based on artificial intelligence relies mainly on supervised learning (i.e., the availability of a ground truth, also called target, for each example of the training dataset). It is difficult, costly, and sometimes impossible to acquire a large dataset of raw data with good quality targets for machine training. Scans to acquire fully sampled data that could be used to generate good quality targets and allow generation of undersampled examples via retrospective undersampling take a long time to acquire per sample. In most of the cases, the patient and/or organs are moving during the scan, resulting in motion artifacts and ultimately bad quality target images. For most use cases, it is not feasible to have fully sampled data, and the target has to be generated by another reconstruction technique such as SENSE or compressed-sensing, which quality limits the achievable performance due to undersampling.

In one approach, supervised and unsupervised learning are mixed (i.e., semi-supervised learning). Classical supervised learning is performed for a subset of the training data, and, for the rest of the training data, a self-consistent loss (e.g., L1 loss) between two predictions of the network: 1) from the original input data, 2) from the same input data but with noise added, is used. Fewer fully sampled training data samples are needed, but are still required. The fully sampled training data may still suffer from motion artifacts, resulting in training to reconstruct images with the artifacts.

SUMMARY

By way of introduction, the preferred embodiments described below include methods, systems, instructions, and computer readable media for reconstruction in medical imaging. Self-consistency using data augmentation is improved by including data consistency. Artificial intelligence is trained based on self-consistency and data consistency, allowing training without supervision. Fully sampled data and/or ground truth is not needed but may be used. The machine-trained model is less likely to reconstruct images with motion artifacts and/or the training data may be more easily gathered by not requiring full sampling.

In a first aspect, a method of machine training is provided for magnetic resonance (MR) reconstruction in medical imaging. MR training data is acquired. Augmentation data is generated from the training data. A neural network is machine trained for the MR reconstruction using the training data and the augmentation data. The training uses (1) a self-consistency loss between pairs of MR training data and/or augmentation data and (2) a data-consistency loss and/or data-consistency constraint. The neural network as machine trained is stored.

In one embodiment, samples of MR k-space data are acquired. Samples of MR k-space data are generated. The neural network is machine trained to output an MR image from input of the MR k-space data.

In another embodiment, the augmentation data is generated with sampling pattern augmentation and/or transposition augmentation. Noise, rotation, or other augmentation may be used. In other embodiments, repetitions for a scan are separated. One of the repetitions is the MR training data and another of the repetitions is the augmentation data for self-consistency loss.

In some approaches, the MR training data is acquired as datasets without full sampling. Some or all of the training data may be fully sampled datasets.

In an embodiment, for each iteration in optimization in machine training, a pair of outputs are generated using the neural network. The pair of outputs are for one of the pairs of MR training data and/or the augmentation data. The self-consistency loss is calculated for the one of the pairs. In this embodiment, the data-consistency loss and/or application of the data-consistency constraint is performed for each of the outputs of the pair.

In some embodiments, the data consistency is integrated into the neural network as a data-consistency constraint. In other embodiments, the data-consistency loss is used. Both constraint and loss for data consistency may be used.

By using data augmentation, self-supervised machine training may be provided. Supervised learning may also be performed, such as supervised machine training the neural network after the self-supervised machine training. In another approach, the self-consistency loss is incorporated as a regularization term in supervised machine training.

In a second aspect, a method is provided for reconstruction of a medical image in a medical imaging system. The medical imaging system scans a patient, resulting in measurements. An image processor reconstructs the medical image from the measurements by applying a machine-learned model. The machine-learned model was trained with both self-consistency and data consistency. The medical image is displayed.

In one embodiment, magnetic resonance scanning is performed so the measurements are k-space data and medical image is a magnetic resonance image.

The machine-learned model may have various embodiments. The machine-learned model may have been trained with self-consistency as a self-consistency loss based on data augmentation. For example, the machine-learned model was trained with self-supervised training using the self-consistency loss where the data augmentation was sampling pattern augmentation and/or transpose augmentation. As another example, the machine-learned model was trained where the data augmentation was division of multiple repetitions in a scan into separate inputs. In another embodiment, the machine-learned model may have been trained with the data consistency being a data consistency loss or may have been trained with the data consistency being a data consistency constraint in an architecture of the machine-learned model. In yet another embodiment, the machine-learned model may have been trained with both self-consistency and data consistency in a first optimization and then supervised learning in a second optimization.

In a third aspect, a system is provided for reconstruction in medical imaging. A medical scanner is configured to scan a patient. An image processor is configured to reconstruct a representation of the patient. The image processor configured to reconstruct by application of a machine-learned model having been trained for the reconstruction based on self-supervised learning from augmentation with data consistency. A display is configured to display an image of the patient. The image is formed from the representation.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

A self-supervised learning technique is provided for deep learning MR or other medical imaging reconstruction. For self-supervised training, a network is trained for reconstruction with a combination of self-consistency loss and a data-consistency loss and/or constraint. Datasets that are not fully sampled may be used to train.

Using standard reconstruction methods (SENSE, CS) for target generations to create ground truth may limit the potential of the deep learning network as the network learns to copy the faults (e.g. smoothing, aliasing, . . . ) of these methods. Instead of relying on the supervised learning paradigm for training a reconstruction neural network, the self-supervised approach does not require (but may still use) fully sample acquisitions. Inclusion of the data consistency allows for training without supervision. Where some of the training data is fully sampled, supervised training may be incorporated, such as fine-tuning using supervised training after self-supervised training or using the self-consistency loss as a regularization.

The self consistency uses data augmentation. Noise augmentation may be used. Other augmentation may be used. For example, multiple repetitions of one scan are used as separate instances, providing augmentation. Various problems may be addressed, such as aliasing and banding artifacts using transposition augmentations. For example, the augmentation is a k-space transposition. As banding and aliasing depend on the orientation of the readout, the network learns to suppress aliasing and banding based on self-consistency. As another example, sample pattern augmentation is used.

During training, the network may learn to be equivariant by transformation. Robustness and out of distribution generalization are added to the network.

Figure 1:
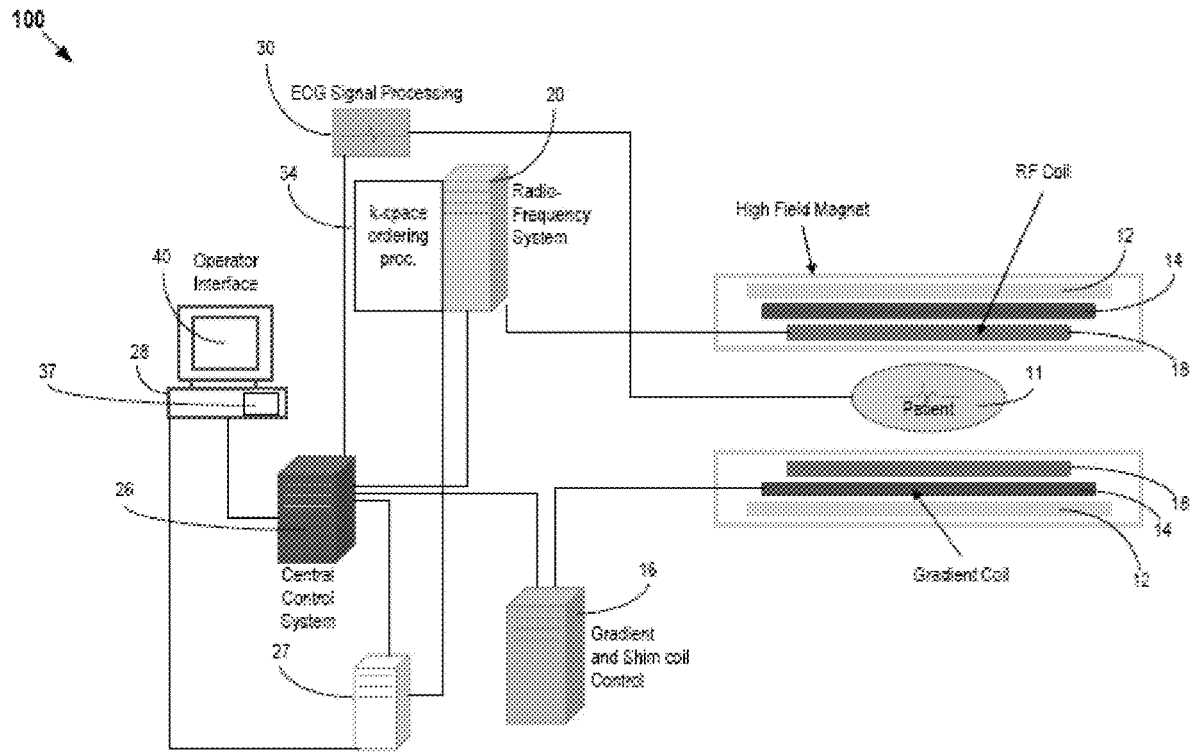
FIG. 1 is a block diagram of an embodiment of an MR system for medical imaging with a self-supervised machine-trained model.

FIG. 1 shows one embodiment of a system for reconstruction in medical imaging. The system scans a given patient and applies a machine-learned model in reconstruction where the model was trained using data consistency and self-consistency. The model for application operates differently than if trained without both data and self-consistency.

The example used herein is in a MR context (i.e., a MR scanner), but the machine-learned model for reconstruction and corresponding type of scanner may be used in reconstruction for computed tomography (CT), positron emission tomography (PET), single photon emission computed tomography (SPECT), or another type of medical imaging.

The system uses a machine-learned model in reconstruction. The machine-learned model is formed from one or more networks and/or another machine-learned architecture (e.g., support vector machine). For example, and used herein, the machine-learned model is a deep-learned neural network. The machine-learned model is used for at least part of the reconstruction, such as for input of k-space data to output an image. In other embodiments, the machine-learned model is used for transform, gradient operation, and/or regularization parts of reconstruction. The reconstruction is of an object or image domain from projections or measurements in another domain, and the machine-learned model is used for at least part of the reconstruction.

The system is implemented by an MR scanner or system, a computer based on data obtained by MR scanning, a server, or another processor. MR scanning system 100 is only exemplary, and a variety of MR scanning systems can be used to collect the MR data. In the embodiment of FIG. 1, the system is or includes the MR scanner or MR system 100. The MR scanner 100 is configured to scan a patient. The scan provides scan data in a scan domain. The system 100 scans a patient to provide k-space measurements (measurements in the frequency domain). In a given scan or examination (e.g., imaging appointment), the patient may be scanned multiple times as part of a protocol providing repetitions or groups of at least partly redundant information. In alternative scans, the patient is scanned once to acquire all the k-space data.

In the system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences.

RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor 34 to provide an MR dataset to an image data processor for processing into an image (i.e., for reconstruction in the object domain from the k-space data in the scan domain). In some embodiments, the image data processor is in or is the central controller, control processor, or control system 26. In other embodiments, such as the one depicted in FIG. 1, the image data processor is in a separate processor 27. ECG synchronization signal generator 30 provides ECG signals used for pulse sequence and imaging synchronization. A two- or three-dimensional k-space storage array of individual data elements in k-space component processor unit 34 stores corresponding individual frequency components forming an MR dataset. The k-space array of individual data elements has a designated center, and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian or another acquisition strategy as the multiple individual frequency components are sequentially acquired during acquisition of an MR dataset representing an MR image. A storage processor in the k-space component processor 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

The central control processor 26 uses information stored in an internal database to process the detected MR signals in a coordinated manner to generate high quality images of a selected slice(s) of the body (e.g., using the image data processor) and adjusts other parameters of the system 100. The stored information includes a predetermined pulse sequence of an imaging protocol and a magnetic field gradient and strength data as well as data indicating timing, orientation, and spatial volume of gradient magnetic fields to be applied in imaging.

The medical scanner 100 is configured by the imaging protocol to scan a region of a patient 11. The same patient 11, without leaving the scanner 100, is scanned, providing scan data based on the protocol. For example, in MR, protocols for scanning a patient for a given examination or appointment include diffusion-weighted imaging, turbo-spin-echo imaging, compressed sensing, contrast imaging with different echo times, parallel sensing, or contrast imaging with different flip angles. Other types of MR or non-MR protocols may be used. The sequential or other scanning results in a set of scan data.

The central control processor 26 (i.e., controller) and/or processor 27 is an image processor that reconstructs a representation of the patient from the k-space data. The image processor is a general processor, digital signal processor, three-dimensional data processor, graphics processing unit, application specific integrated circuit, field programmable gate array, artificial intelligence processor, tensor processor, digital circuit, analog circuit, combinations thereof, or another now known or later developed device for reconstruction. The image processor is a single device, a plurality of devices, or a network. For more than one device, parallel or sequential division of processing may be used. Different devices making up the image processor may perform different functions, such as reconstructing by one device and volume rendering by another device. In one embodiment, the image processor is a control processor or other processor of the MR scanner 100. Other image processors of the MR scanner 100 or external to the MR scanner 100 may be used.

The image processor is configured by software, firmware, and/or hardware to reconstruct. The image processor operates pursuant to instructions stored on a non-transitory medium to perform various acts described herein.

The image processor is configured to reconstruct a representation in an object domain. The object domain is an image space and corresponds to the spatial distribution of the patient. A planar or volume representation is reconstructed as an image representing the patient. For example, pixels values representing tissue in an area or voxel values representing tissue distributed in a volume are generated.

The representation in the object domain is reconstructed from the scan data in the scan domain. The scan data is a set or frame of k-space data from a scan of the patient. The protocol for a scan of a patient may generate multiple such sets or frames of k-space (scan) data. For each repetition, the k-space measurements resulting from the scan sequence are transformed from the frequency domain to the spatial domain in reconstruction. In one approach, reconstruction for a given repetition is an iterative process, such as a minimization problem. In some embodiments, an unrolled iterative reconstruction is provided as a network or model of iteration sequences. A given iteration either in an unrolled network or through a repetition of the reconstruction operations includes a gradient update and regularization. The gradient update compares the current image object with the scan data (e.g., k-space measurements). This comparison uses a system transform to relate the measurements to the image object, such as a data consistency verification. Any gradient or comparison relating the image object to the measurements may be used.

Regularization is provided in one, some, or all the iterations. Other filtering and/or operations for reconstruction and/or post-reconstruction may be provided. Input bias field correction and/or extrapolation for momentum may be provided as part of the reconstruction. In other embodiments, the reconstruction is performed without iteration and/or gradient update.

The image processor is configured to reconstruct a representation of the patient. The reconstruction uses application of a machine-learned model having been trained for the reconstruction based on self-supervised learning from augmentation with data consistency. The training of the machine-learned model results in values for learnable (learned) parameters. By using both data consistency and self-consistency in training, different learned values of the machine-learned model result than if a different losses and/or constraints where used.

The resulting representation may be a complex or real image. The output image is the final reconstructed image. The output image represents the patient (i.e., a reconstructed representation). The image processor may be configured to generate an MR image. Where the representation is of an area, the values of the representation may be mapped to display values (e.g., scalar values to display color values) and/or formatted (e.g., interpolated to a display pixel grid). Alternatively, the output representation is of display values in the display format. Where the representation is of a volume, the image processor performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

A generated display image of the reconstructed representation or image for a given patient is presented on a display 40 of the operator interface. The computer 28 of the operator interface includes a graphical user interface (GUI) enabling user interaction with central control processor 26 and enables user modification of magnetic resonance imaging signals in substantially real time. The display processor 37 processes the magnetic resonance signals to provide image representative data for display on display 40, for example.

The display 40 is a CRT, LCD, plasma, projector, printer, or other display device. The display 40 is configured by loading an image to a display plane or buffer. The display 40 is configured to display the reconstructed MR image of the region of the patient.

Figure 2:
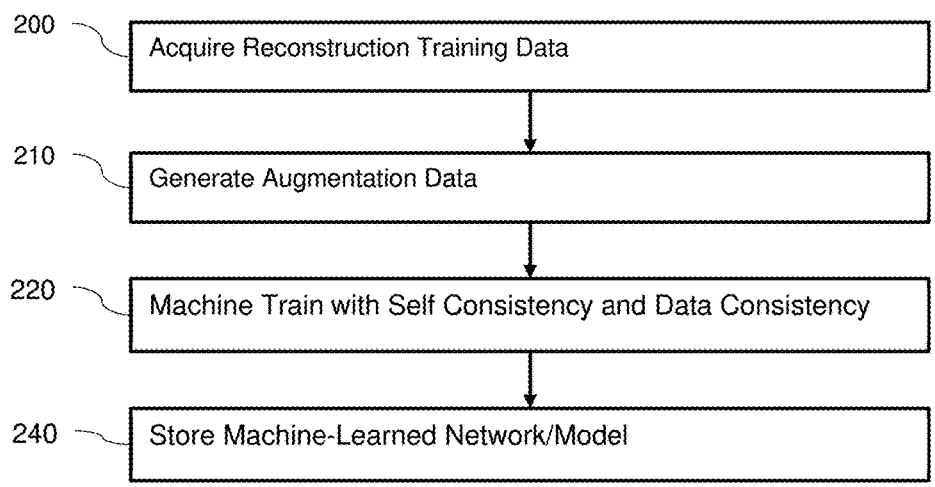
FIG. 2 is a flow chart diagram of one embodiment of a method for machine training for reconstruction using self-consistency and data consistency.

FIG. 2 is a flow chart diagram of one embodiment of a method for machine training for reconstruction in medical imaging, such as training a neural network used in MR reconstruction from signals collected by an MR scanner. Once trained, the machine-learned model may be used with the same learned values in reconstruction of representations for any number of patients from a respective number of sets of MR scan data for the patients.

The method is implemented by a computer, such as a personal computer, workstation, and/or server. Other computers may be configured to perform the acts of FIG. 2. The MR scanner 100 or central control processor 26 may implement the method. In one embodiment, the computer and a database are used to machine train and store the samples, augmented data, training data, output images, and the resulting final trained model. The stored model is then distributed to one or more MR scanners 100 for application using the model as fixed (i.e., the learned values of the variables are not changed for reconstructions for a given patient and/or for different patients).

The method is performed in the order shown (i.e., top to bottom or numerical). Additional, different, or fewer acts may be provided. For example, instead of or in addition to storing in act 240, the machine-learned model is applied to previously unseen scan data for a patient in a reconstruction as shown in FIG. 8. As another example, an act for gathering or creating training data is performed. In yet another example, act 210 is part of act 200, such as the augmented data being training data.

In act 200, training data is acquired. The training data is acquired from memory, scanning, or transfer. To machine train, training data is created, gathered, or accessed.

The training data includes many sets of data, such as MR k-space data in sets. Tens, hundreds, or thousands of sample scan data are acquired, such as from scans of patients, scans of phantoms, simulation of scanning, and/or by image processing to create further samples. Many examples that may result from different scan settings, patient anatomy, scanner characteristics, or other variance that results in different samples in scanning are used. In one embodiment, an already gathered or created MR dataset is used for the training data.

The samples are from scanning or simulation following one or more protocols. The scanning may be for fully sampling the patient. In other embodiments, the scanning follows a protocol that only partially samples (i.e., without full sampling), such as diffusion-weighted, contrast (e.g., different echo times or flip angles), compressed sensing, parallel imaging, and/or turbo-spin-echo imaging. Depending on the role in reconstruction of the model to be machine trained, the training data may use k-space data or image domain data for the samples. The samples are used in deep learning to determine the values of the learnable variables (e.g., values for convolution kernels) that produce outputs with minimized cost function across the variance of the different samples.

For self-supervised machine learning, the training data may not include ground truth information. For example, desired images from the input samples (e.g., k-space data) are not provided for training. Data consistency and self-consistency allow for training without ground truth images. In alternative embodiments, the training data includes ground truth information. 1, 5, 10, 25, 50, 75 or other percentage of the samples of the training data include ground truth images. The desired representation or image resulting from a given sample is provided.

In act 210, the image processor generates augmentation data. The data may be generated by loading from memory and/or by creating the data from other training data. In other embodiments, the augmentation data was previously created and stored or provided with or as part of the training data.

Self-consistency seeks to generate the same image despite variation in a given input. A self-consistency loss is used in training so that the model learns to reconstruct the same or similar image despite variation in the same input. The model being machine trained generates an output for one sample and an output for another sample where the two samples differ by the augmentation. The same training data sample with and without augmentation is applied to the model in training, and the two resulting outputs are compared to train the model to be self-consistent despite the variation from the augmentation. The self-consistency loss is used to train the network to be robust to data augmentation (i.e., train the network to be augmentation invariant).

The scheme uses data augmentation to produce two different network outputs that are trained to be similar. To generate the augmentation data, the samples are augmented to create variance. For example, noise is added the input samples (e.g., noise in k-space). The added noise may be from system, scan, and/or patient modeling, may be experimentally determined noise, and/or may be randomly generated. As another example, rotation is applied. The training data is augmented with rotated samples. Any physics of the input data or samples may be varied.

In one embodiment, the image processor applies sampling pattern augmentation. The sampling pattern is varied. For example, ipat factor augmenation and/or center lines augmentation is used. The sampling may be varied, such as using every other, every third, or every N lines where N is a non-zero positive integer. Partial Fourier (e.g., sampling less than all available frequencies) sampling may be used. As another example, the low frequency center lines are removed or not included in the sampling.

In another embodiment, transposition augmentation is used. For transposition augmentation, the input k-space data is transposed while the sampling mask is not. The resulting predicted image (output from the network) is then transposed back to its initial orientation in order to be compared in the loss with the target image or another predicted image. The effect of transposing the image with respect to the sampling mask is that artifacts such as aliasing and banding are also transposed, and thus training the network with such augmentation scheme is a good way to get rid of these artifacts as the network leans to be invariant to these augmentations.

In yet another embodiment, scans using repetitions are used to generate the augmentation. One or more of the repetitions are separated, providing multiple samples as the augmentation. Rather than using the repetitions together in a given or single scan, the repetitions are separated where different subsets are used as the training samples (e.g., training data and augmentation for that training data). If multiple repetitions of one scan are available, different repetitions of the scan can be used for each of the multiple network predictions used in the self-supervised loss.

The augmentation creates different samples from the same data. For example, two thousand samples are provided as initial training data. These samples are from different scans. The same augmentation is generated for each sample, resulting in four thousand samples or two thousand pairs of samples. Different types of augmentation may be applied to different samples or the same samples. For example, multiple augmentations (e.g., noise and sample pattern) are applied to a given sample, resulting in a pair of the original sample and the augmented sample that includes a different sampling pattern and added noise. Any combination of one or more types of augmentation for a given augmented sample and creation of different numbers of pairs with different augmentation may be used. Both members of each pair may be augmented and/or one member is the original training data and the other member is augmented from the original training data. The acquisition in act 200 provides an original set of samples. This set is used to form pairs of samples to be used in training using the augmentation in act 210. The pairs are used for training using self-supervision where the outputs based on inputs from the pairs are used as a loss in self consistency check to train. Each pair is based on a same sample.

In act 220, a computer (e.g., image processor) or another machine trains a model for reconstruction, such as training a neural network for regularization, gradient, Fourier transform, or k-space-to-final-image operations. The neural network is machine trained for MR reconstruction using the training data and/or augmentation data, including many input samples of sets of scan data with or without corresponding ground truth outputs.

In one embodiment, deep learning is used to train the model. The training learns both the features of the input data and the conversion of those features to the desired output (i.e., denoised or regularized image domain data). Backpropagation, RMSprop, ADAM, or another optimization is used in learning the values of the learnable parameters of the network (e.g., the convolutional neural network (CNN) or fully connection network (FCN)). For self-supervised learning, the differences (e.g., L1, L2, mean square error, or other loss) between the estimated outputs for both inputs of each sample pair are minimized. To avoid trivial solutions (e.g., learning to generate a constant output no matter the input), another loss or constraint is used, such as data consistency.

Any architecture or layer structure for machine learning to perform an operation for reconstruction may be used. For example, a hierarchal, unrolled, and/or iterative architecture to regularize in reconstruction may be used. As another example, an architecture for input of k-space data and output of reconstructed object space (e.g., image) is defined. The architecture defines the structure, learnable parameters, and relationships between parameters. In one embodiment, a convolutional or another neural network is used. Any number of layers and nodes within layers may be used. A DenseNet, U-Net, encoder-decoder, Deep Iterative Down-Up CNN, image-to-image, and/or another network may be used. Some of the network may include dense blocks (i.e., multiple layers in sequence outputting to the next layer as well as the final layer in the dense block). Down sampling and up sampling layers may be included. Skip connections may be used. Any know known or later developed neural network may be used. Any number of hidden layers and/or nodes may be provided between the input layer and output layer.

For iterative reconstruction, the architecture may include an unrolled arrangement of layers or iterative optimization. The same network is trained to be used for each repetition or iterations. Alternatively, a different network is provided for each repetition in an unrolled embodiment, whether a different architecture or same architecture but with different values for one or more of the learnable parameters of the network. Different networks are trained for reconstruction for different repetitions.

The neural network is trained for MR reconstruction to output an image. In response to input scan data, the reconstruction outputs an image. The network is to be trained to perform some aspect of this reconstruction. As a result, an image may be output as an MR reconstruction in training. For each pair of training samples, each member of the pair is input to generate an output using the current values of the learnable parameters. For example, a first sample of k-space data from a scan from the training data is input, and the model being trained outputs a first image. Another sample augmented from the same first sample (e.g., k-space data with transpose, noise added, rotated, and/or altered sample pattern) is input, and the model being trained outputs a second image. These two images are compared for optimizing the values of the learnable parameters to minimize the difference between the images of the input pairs across the many samples. Using the many pairs of samples and optimization, the values of the learnable parameters are adjusted based on the performance of the model being trained and the losses.

The machine training uses a loss or losses to learn the values of the learnable parameters. The loss is based, at least, in part, on the outputs from the pairs of sample inputs. This is a self-consistency loss. The output images or another reconstruction of each pair based on the same training data sample are compared. The loss is calculated from or as part of the comparison. The difference between the images from the pairs are to be minimized. Any function representing difference between two images or reconstructions may be used, such as L1 or L2. In an alternative embodiment, an adversarial network is trained to determine whether two images are the same or not, and the output of the adversarial network is used as the loss (i.e., a generative adversarial network and corresponding training is used).

For the self-supervised machine training, the training uses (1) a self-consistency loss between pairs of MR training data and/or augmentation data. For each iteration in optimization, a pair of outputs are generated using the neural network or other model. The pair of outputs are based on the same scan or sample. For example, one of the pairs of MR training data and the augmentation data is used. The self-consistency loss is calculated for each one of the pairs (i.e., loss between the two images output from the reconstruction in response to the input from the same sample altered by augmentation). The self-consistency loss is used to train the network to be robust to data augmentation (i.e., train the network to be augmentation invariant). The effects noise, rotation, sample pattern, transposition, and/or another augmentation is minimized. Data augmentation of act 210 is used to produce two different network outputs, and the network is trained in act 220 so that thow two outputs are similar.

Figure 3:
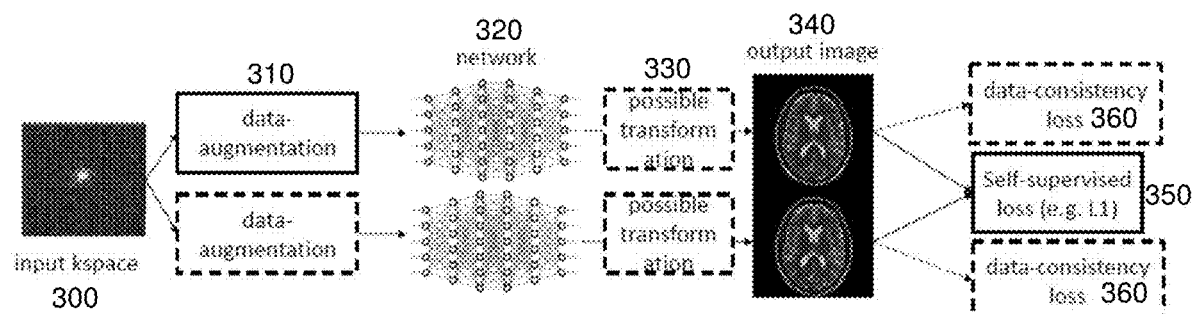
FIG. 3 illustrates an example of machine training using self-consistency loss and data-consistency loss.

FIG. 3 shows an example. A sample 300 of input k-space data from a scan is provided. The sample is augmented, resulting in a pair 310 of augmented data. One member of the pair may be non-augmented (i.e., the original sample) or both members may be augmented but differently. The network 320 being trained is represented twice but is the same network used in parallel or sequentially. The network 320 outputs the pair of images 340 used for the self-supervised loss 350 (self-consistency loss).

In training, the data augmentation may be a transformation 330. This transformation after the inference by the network 320 is used to transform the reconstructed outputs differently. The transformation 330 is used instead of or in addition to invariance from the augmentation 310 before inference where equivariance (e.g., for rotation or transposition) is desired.

In self-supervised learning, in addition to data augmentation invariance, it is important to impose another property in order to avoid trivial solutions (e.g., the network generating a constant output, which would produce a zero self-consistency loss). In one embodiment, a data-consistency loss or constraint is used to avoid the trivial solutions. The training uses both (1) the self-consistency loss between pairs of MR training data and/or augmentation data and (2) a data-consistency loss and/or data-consistency constraint. Other unsupervised losses or constraints may be used. In alternative embodiments, a loss based on comparison to ground truth (i.e., supervised training) is included.

FIG. 3 shows an example using a data consistency loss 360. For each of the output images 340 of a pair of inputs, a data-consistency loss is calculated. The output, x, is transformed by a forward model, A. The resulting transform is compared (difference) to the input (e.g., k-space data of the member of the pair) y (i.e., $\|AX-Y\|$). This difference is a loss based on data consistency. Various comparisons or difference functions may be used, such as L1 or L2.

The two losses 360 for the two outputs of a pair are summed, averaged, weighted averaged, or otherwise combined. Similarly, the two different types of losses where data-consistency loss is used, are summed, averaged, weighted averaged, or otherwise combined (e.g., average data consistency loss 360 averaged with the self-supervised loss 350). Any combination of losses may be used.

As an alternative to calculating the data-consistency loss, the data consistency may be included as a constraint. The constraint is applied to the output generated in response to any input. The constraint in built into or included in the architecture of the model being trained. For example, one or more layers of a neural network, such as a layer immediately prior to the output layer or the output layer enforces data-consistency. A gradient update with step size of one at the end of the network enforces the data-consistency term $\|AX-Y\|$ to be small. This constraint layer alters the image to be output so that the constraint is satisfied. Data-consistency layers can be used in the network in an unrolled type of architecture where data-consistency layers alternate with regularization layers or are performed in parallel. These data-consistency layers can have trainable parameters (e.g. for the gradient step-size and/or the extrapolation step-size) and tend to improve data-consistency due to their architecture.

The self-consistency loss and data consistency (loss and/or constraint) are used in unsupervised training. Ground truth is not needed as the losses are based on the performance of the model being trained and/or the input data. This self-supervised approach allows use of samples without ground truth and/or samples based on scans without full sampling in the scan.

Semi-supervised training may be used. Ground truth may be available for some of the samples (i.e., supervised dataset). In one embodiment, sequential training is applied. Supervised machine training with a loss based on a difference of the output from the ground truth (i.e., no need for input pairs) is performed after training the model with the self-supervised training. If a small supervised dataset (e.g., 5-30% of the samples) corresponding to the final reconstruction application is available, the model is fined tuned on that dataset with ground truth after the self-supervised learning training.

In another embodiment, the self-consistency loss is a regularization term in supervised machine training. The data consistency may or may not be used as the loss from ground truth may avoid trivial solutions. If a large supervised dataset (e.g., 50% or more) is available, the self-consistency loss with data augmentation is used as a regularization term (i.e., in addition to the supervised learning loss). This could increase the distribution generalization of the model and also remove some potential artifacts (e.g., using self-supervised loss with transpose augmentation should remove potential aliasing and banding artefacts without having to use a generative adversarial network).

Machine learning is an offline training phase where the goal is to identify an optimal set of values of learnable parameters of the model that can be applied to many different inputs. These machine-learned parameters can subsequently be used during clinical operation to reconstruct. Once learned, the machine-learned model is used in an online processing phase (application or testing) in which scan data from a scan is reconstructed into an image. For example, once trained, the neural network 320 is applied in reconstruction of a representation or image of a patient from a scan of that patient.

In act 240 of FIG. 2, the computer or image processor stores the machine-learned model resulting from the machine learning. For example, the machine-learned neural network 320 is stored. The machine-learned model is saved in memory. After training, the machine-learned model or models are represented as a matrix, filter kernels, and/or architecture with the learned values. The learned convolution kernels, weights, connections, and/or layers of the neural network or networks are provided and stored. The machine-learned model may be stored locally or transferred over a network or by moving the memory to other computers, workstations, and/or MR scanners.

The model resulting from the machine training using the plurality of the samples is stored. This stored model has fixed weights or values of learnable parameters determined based on the machine training. These weights or values are not altered by patient-to-patient or over multiple uses for different medical scans. The weights or values are fixed, at least over a number of uses and/or patients. The same weights or values are used for different scans corresponding to different patients and/or different examinations or appointments. The same values or weights may be used by different medical scanners. The fixed machine-learned model or models are to be applied without needing to train as part of the application. Re-training or updated training may be provided.

Figure 4:
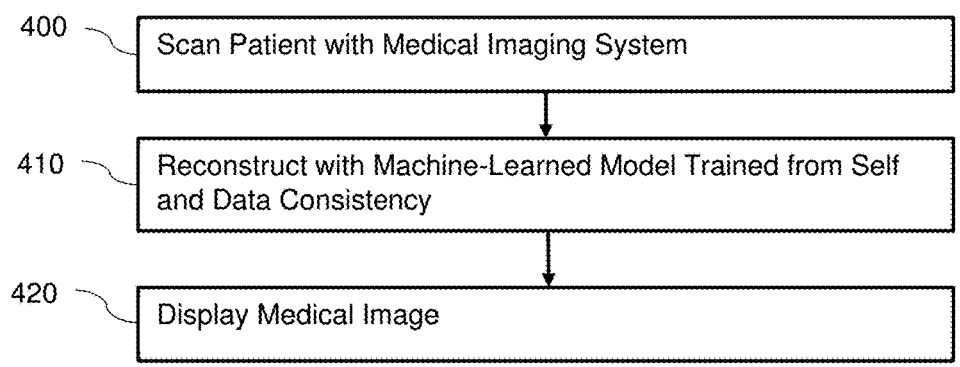
FIG. 4 is a flow chart diagram of one embodiment of a method for reconstruction using a machine-learned network having been trained with self and data consistency.

FIG. 4 is a flow chart diagram of one embodiment of a method for reconstruction of a medical image in a medical imaging system, such as reconstruction of a MR image in an MR system. A machine-learned model as trained is applied for at least part of the reconstruction operation. Once trained, the machine-learned model is used in reconstruction of a spatial representation (e.g., image) from input k-space measurements for a patient. The application is part of scanning and reconstruction for patient diagnosis of a given patient for a given examination, scan, and/or appointment. The machine-learned model was previously trained using a combination of self-consistency loss and another loss or constraint (e.g., data-consistency).

During application to one or more different patients and corresponding different scan data, the same learned weights or values are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient.

The method is performed by the system of FIG. 1 or another system. The medical scanner scans the patient. An image processor reconstructs the image using the machine-trained model. A display displays the medical image resulting from the reconstruction. Other components may be used, such as a remote server or a workstation performing the reconstruction and/or display.

The method is performed in the order shown or other orders. Additional, different, or fewer acts may be provided. For example, a preset, default, or user input settings are used to configure the scanning prior art act 400. As another example, the image is stored in a memory (e.g., computerized patient medical record) or transmitted over a computer network instead of or in addition to the display of act 420.

In act 400, the medical imaging system scans a patient. The scan is guided by a protocol, such as diffusion-weighted, contrast, or turbo-spin-echo protocol. The scanning results in measurements. In an MR example, a pulse sequence is created based on the configuration of the MR scanner (e.g., the imaging protocol selected). The pulse sequence is transmitted from coils into the patient. The resulting responses are measured by receiving radio frequency signals at the same or different coils. The scanning results in k-space measurements as the scan data. Scan data for different repetitions in the same scan (i.e., scanning the same region multiple times) may be acquired for some protocols.

In act 410, an image processor reconstructs a representation of the patient from the scan data. The image processor reconstructs a medical image in the form of a display image (i.e., formatted for display), a volume image (i.e., voxels), or an area or plane image (i.e., planar representation). For MR reconstruction, the k-space data is Fourier transformed into scalar values representing different spatial locations, such as spatial locations representing a plane through or volume of a region in the patient. Scalar pixel or voxel values are reconstructed as the MR image. The spatial distribution of measurements in object or image space is formed. This spatial distribution is an image representing the patient.

Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image. In alternative embodiments, the machine-learned network outputs the display image directly in response to the input.

The reconstruction is performed, at least in part, using a machine-learned model, such as a neural network trained with deep machine learning. The machine-learned model is previously trained, and then applied as trained in reconstruction. Fixed values of learned parameters are used for application. In application of the already trained network, the reconstruction process is followed. The machine-learned model is used in the reconstruction, such as performing a transform, gradient updated, regularization, and/or combination thereof. In one embodiment, the machine-learned model receives input of k-space data from a scan and outputs the reconstructed MR image. In other embodiments, other models and/or algorithms are used with application of the machine-learned model to reconstruct the MR image from the k-space data. In response to the input of the scan data for a given repetition for a given patient, a patient specific image is reconstructed. The machine-learned model may output the image as pixels, voxels, and/or a display formatted image in response to the input or be used in another way in the reconstruction. The learned values and network architecture, with any algorithms (e.g., extrapolation and gradient update) determine the output from the input.

The machine-learned model was previously trained based on a loss function from self-consistency plus another loss or constraint, such as data consistency. For example, the machine-learned model was trained with both self-consistency and data consistency. The information used in training results in a particular model that operates in a particular way so that an output is generated in response to an input in application that would vary given other information used in training.

The machine-learned model was trained with self-consistency as a self-consistency loss based on data augmentation. Self-supervised training using the self-consistency loss was used. The data augmentation for the self-supervised training may be noise, rotation, sampling pattern, transpose and/or another augmentation. The data augmentation for the self-supervised training may be additionally or alternatively division of multiple repetitions in a scan into separate inputs.

In one embodiment, the machine-learned model was trained with the data consistency being a data consistency loss. Using a combination of the self-consistency loss and the data-consistency loss, the training resulted in the values of the learnable parameters being applied. In another embodiment, the machine-learned model was trained with the data consistency being a data consistency constraint in an architecture of the machine-learned model. The training resulted in a layer or layers enforcing data consistency. This layer or layers, in addition to having been used and learned in training, are applied as part of the model during application for a given patient.

The training and resulting model being applied may have included at least some supervised learning. For example, the machine-learned model was trained with both self-consistency and data consistency in a first optimization and then supervised learning in a second optimization (i.e., supervised learning with ground truth images) used to fine-tune or refine the self-supervision-trained model. As another example, the self-supervision was used in training as a regularizer during supervised training.

In act 420, a display (e.g., display screen or device) displays the medical image, such as the MR image. The medical image, after or as part of any post processing, is formatted for display on the display. The display presents the image for viewing by the user, radiologist, physician, clinician, and/or patient. The image assists in diagnosis.

The displayed image may represent a planar region or area in the patient. Alternatively, or additionally, the displayed image is a volume or surface rendering from voxels (three-dimensional distribution) to the two-dimensional display.

The same deep machine-learned model may be used for different patients. The same or different copies of the same machine-learned model are applied for different patients, resulting in reconstruction of patient-specific representations or reconstructions using the same values or weights of the learned parameters of the model. Different patients and/or the same patient at a different time may be scanned while the same or fixed trained machine-learned regularization model is used in reconstruction the image. Other copies of the same deep machine-learned model may be used for other patients with the same or different scan settings and corresponding sampling or under sampling in k-space.

Although the subject matter has been described in terms of exemplary embodiments, it is not limited thereto. Rather, the appended claims should be construed broadly, to include other variants and embodiments, which can be made by those skilled in the art.

What is claimed is:

1. A method of machine training for magnetic resonance (MR) reconstruction in medical imaging, the method comprising:
    acquiring MR training data;
    generating augmentation data from the MR training data;
    machine training a neural network for the MR reconstruction using the MR training data and the augmentation data, wherein the machine training generates an output for each of the pairs of the MR training data and/or augmentation data and uses (1) a self-consistency loss between the respective output pairs and (2) a data-consistency loss and/or data-consistency constraint; and
    storing the neural network as machine trained.

2. The method of claim 1 wherein acquiring comprises acquiring samples of MR k-space data, wherein generating comprises generating samples of MR k-space data, and wherein machine training comprises training the neural network to output an MR image from input of the MR k-space data.

3. The method of claim 1 wherein generating the augmentation data comprises generating sampling pattern augmentation and/or transposition augmentation.

4. The method of claim 1 wherein generating the augmentation data comprises separating repetitions for a scan, one of the repetitions being the MR training data and another of the repetitions being the augmentation data.

5. The method of claim 1 wherein acquiring comprises acquiring the MR training data as datasets without full sampling.

6. The method of claim 1 wherein machine training comprises calculating the data-consistency loss and/or applying the data-consistency constraint for each of the outputs of the pair.

7. The method of claim 1 wherein machine training comprises using the data-consistency constraint as integrated into the neural network.

8. The method of claim 1 wherein machine training comprises using the data-consistency loss.

9. The method of claim 1 wherein machine training comprises self-supervised machine training.

10. The method of claim 9 further comprising supervised machine training the neural network after the self-supervised machine training.

11. The method of claim 1 wherein machine training comprises incorporating the self-consistency loss as a regularization term in supervised machine training.

12. A method for reconstruction of a medical image in a medical imaging system, the method comprising:
    scanning, by the medical imaging system, a patient, the scanning resulting in measurements;
    reconstructing, by an image processor applying a machine-learned model, the medical image from the measurements, the machine-learned model having been trained with both self-consistency and data consistency enforcement using outputs of the machine-learned model when input pairs of sample data, wherein at least one of the sample data is augmented; and
    displaying the medical image.

13. The method of claim 12 wherein scanning comprises magnetic resonance scanning, the measurements comprise k-space data, and the medical image comprises a magnetic resonance image.

14. The method of claim 12 wherein reconstructing comprises reconstructing by application of the machine-learned model, the machine-learned model having been trained with self-consistency as a self-consistency loss based on data augmentation.

15. The method of claim 14 wherein reconstructing comprises reconstructing by the application of the machine-learned model, the machine-learned model having been trained with self-supervised training using the self-consistency loss where the data augmentation was sampling pattern augmentation and/or transpose augmentation.

16. The method of claim 14 wherein reconstructing comprises reconstructing by the application of the machine-learned model, the machine-learned model having been trained where the data augmentation was division of multiple scan repetitions into separate inputs.

17. The method of claim 12 wherein reconstructing comprises reconstructing by application of the machine-learned model, the machine-learned model having been trained with the data consistency being a data consistency constraint in an architecture of the machine-learned model or a data consistency loss.

18. The method of claim 12 wherein reconstructing comprises reconstructing by application of the machine-learned model, the machine-learned model having been trained with both self-consistency and data consistency in a first optimization and then supervised learning in a second optimization.

19. A system for reconstruction in medical imaging, the system comprising:
    a medical scanner configured to scan a patient;
    an image processor configured to reconstruct a representation of the patient, the image processor configured to reconstruct by application of a machine-learned model having been trained for the reconstruction based on self-supervised learning with data consistency and self-consistency enforcement using outputs of the machine-learned model when input pairs of sample data, wherein at least one of the sample data is augmented; and
    a display configured to display an image of the patient, the image formed from the representation.

* * * * *